(12) United States Patent
Ferreira dos Santos da Fonseca et al.

(10) Patent No.: US 10,624,574 B2
(45) Date of Patent: Apr. 21, 2020

(54) DETERMINATION SYSTEM AND METHOD FOR DETERMINING A SLEEP STAGE OF A SUBJECT

(71) Applicant: KONINKLIJKE PHILIPS N.V., Eindhoven (NL)

(72) Inventors: Pedro Miguel Ferreira dos Santos da Fonseca, Borgerhout (BE); Carmina Avezedo, Oporto (PT)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/310,441

(22) PCT Filed: Jun. 17, 2017

(86) PCT No.: PCT/EP2017/064856
§ 371 (c)(1),
(2) Date: Dec. 16, 2018

(87) PCT Pub. No.: WO2018/001758
PCT Pub. Date: Jan. 4, 2018

(65) Prior Publication Data
US 2019/0183414 A1 Jun. 20, 2019

(30) Foreign Application Priority Data
Jun. 27, 2016 (EP) .................. 16176468

(51) Int. Cl.
*A61B 5/00* (2006.01)
*A61B 5/0205* (2006.01)
(Continued)

(52) U.S. Cl.
CPC .......... *A61B 5/4812* (2013.01); *A61B 5/0205* (2013.01); *A61B 5/0402* (2013.01);
(Continued)

(58) Field of Classification Search
CPC .... A61B 5/0205; A61B 5/0402; A61B 5/0456
See application file for complete search history.

(56) References Cited

U.S. PATENT DOCUMENTS 7,460,899 B2 * 12/2008 Almen ............... A61B 5/02405
340/575
2008/0306351 A1 12/2008 Izumi
(Continued)

FOREIGN PATENT DOCUMENTS

| CN | 104720746 A | 6/2015 |
| WO | 2006054306 A2 | 5/2006 |
| WO | 2010140117 A1 | 12/2010 |

OTHER PUBLICATIONS

Mack, et al., "Sleep Assessment using a Passive Ballistocardiography-Based System: Preliminary Validation", 31st Annual International Conference of the IEEE Engineering in Medicine and Biology Society: Engineering The Future of Biomedicine, Sep. 3, 2009, pp. 4319-4322.
(Continued)

*Primary Examiner* — Lynsey C Eiseman
*Assistant Examiner* — Amanda L. Steinberg

(57) ABSTRACT

The present invention relates to a determination system, a corresponding determination method and a computer program for determining a sleep stage of a subject. The determination system comprises a cardiorespiratory signal providing unit (10), an actigraphy data providing unit (20), a first sleep stage determination unit (30) for determining the sleep stage based on a cardiorespiratory signal, and a second sleep stage determination unit (40) for determining the sleep stage based on actigraphy data. The first sleep stage determination unit (30) determines a sleep onset latency (SOL) of the subject. The sleep stage of the subject is determined using the first sleep stage determination unit (30) up to the SOL and the second sleep stage determination unit (40) after
(Continued)

the SOL. The determination system and corresponding method allow for a more reliable determination of a sleep stage of subject, in particular improve the determination of the SOL of the subject.

15 Claims, 5 Drawing Sheets

(51) Int. Cl.

| | | |
|---|---|---|
| *A61B 5/11* | (2006.01) | |
| *A61B 5/0402* | (2006.01) | |
| *A61B 5/0456* | (2006.01) | |
| *G01S 7/41* | (2006.01) | |
| *A61B 5/024* | (2006.01) | |
| *A61B 5/08* | (2006.01) | |

(52) U.S. Cl.
CPC .......... *A61B 5/0456* (2013.01); *A61B 5/1102* (2013.01); *A61B 5/1118* (2013.01); *A61B 5/681* (2013.01); *A61B 5/7267* (2013.01); *G01S 7/415* (2013.01); *A61B 5/02416* (2013.01); *A61B 5/0816* (2013.01); *A61B 5/4809* (2013.01); *A61B 2562/0219* (2013.01)

(56) References Cited

U.S. PATENT DOCUMENTS

| | | |
|---|---|---|
| 2009/0203972 A1 | 8/2009 | Heneghan et al. |
| 2011/0034811 A1 | 2/2011 | Naujokat et al. |
| 2011/0092831 A1 | 4/2011 | Herscovici-Cohen et al. |
| 2014/0088378 A1 | 3/2014 | Muzet |
| 2014/0275852 A1* | 9/2014 | Hong ................. A61B 5/02427 600/301 |
| 2014/0371547 A1 | 12/2014 | Gertenberg et al. |
| 2015/0190086 A1 | 7/2015 | Chan et al. |
| 2016/0007931 A1 | 1/2016 | Rubin et al. |
| 2016/0374569 A1* | 12/2016 | Breslow ............. A61B 5/02405 600/301 |
| 2017/0360308 A1 | 12/2017 | Fonseca et al. |

OTHER PUBLICATIONS

Meltzer, et al., "Comparison of actigraphy immobility rules with polysomnographic sleep onset latency in children and adolescents", Sleep and Breathing, vol. 19, No. 4, Feb. 17, 2015, pp. 1415-1423.

Fonseca, et al., "Sleep stage classification with ECG and respiratory effort", Physiological Measurement, 36 (2015), pp. 2027-2040.

Klosch, et al., "The SIESTA Project Polygraphic and Clinical Database", A New Approach to Studying Subjective and Objective Measurements of Human Sleep, IEEE Engineering in Medicine and Biology, May/Jun. 2001, pp. 51-57.

Long, et al., "Sleep and Wake Classification with Actigraphy and Respiratory Effort Using Dynamic Warping", IEEE Journal of Biomedical and Health Informatics, vol. XX, No. XX, XXXX, 2013, pp. 1-12.

Hall, M., "Correlation-based Feature Selection for Machine Learning", Thesis submitted for degree of Doctor of Philosophy at the University of Waikato, Department of Computer Science, Hamilton, New Zealand, 198 pages.

Devot, et al., "Sleep/Wake Detection Based on Cardiorespiratory Signals and Actigraphy", 32nd Annual International Conference of the IEEE EMBS, Buenos Aires, Argentina, Aug. 31-Sep. 4, 2010, pp. 5089-5092.

Willemen, et al., "An evaluation of cardio-respiratory and movement features with respect to sleep stage classification", pp. 1-9 (Abstract).

\* cited by examiner

DETERMINATION SYSTEM AND METHOD FOR DETERMINING A SLEEP STAGE OF A SUBJECT

This application is the U.S. National Phase application under 35 U.S.C. § 371 of International Application No. PCT/EP2017/064856, filed on Jun. 17, 2017, which claims the benefit of European Application Serial No. 16176468.3, filed Jun. 27, 2016. These applications are hereby incorporated by reference herein.

FIELD OF THE INVENTION

The present invention relates to a determination system for determining a sleep stage of a subject. In particular, it relates to determination system, a determination method and a computer program for determining a sleep stage of a subject. It finds application in detecting sleep and wake periods and the sleep onset latency based on body movements and cardiorespiratory activity of the subject. However, it is to be understood that the present invention also finds application in other fields and it is not necessarily limited to the above mentioned application.

BACKGROUND OF THE INVENTION

Automatic sleep stage classification allows for real-time sleep staging and remote monitoring of subjects. One of the parameters of interest derived from sleep stages is called sleep onset latency (SOL) which is an indicator in the evaluation of sleep complaints and also in the evaluation of sleep disorders such as insomnia and circadian rhythm disorders. The SOL basically measures the amount of time elapsed between the instant when the subject wishes to sleep until the moment when that subject eventually falls asleep.

It is known to determine SOL by classifying periods of wake and sleep and then, for instance, determining SOL as the amount of time before a certain criterion is determined, for instance, until the first occurrence of three consecutive epochs classified as sleep.

Actigraphy devices are employed to detect periods of wake and sleep based on body movements of the subject. While these body movements are indicative for brief periods of awakening during sleep since these occur together with body movements, this is not always valid at the beginning of the night, in particular for determining the SOL. Since subjects, particularly subjects suffering from a long SOL, try to lay as still as possible, actigraphy based SOL estimates underestimate the SOL.

WO 2010/140117 A1 discloses a method for the automatic assessment of the presence/severity of the sleep problem and its exact nature. The assessment is based on qualitative information about sleep patterns, insomnia-related factors and daytime consequences, as well as quantitative information about sleep patterns measured by a sensor. Multiple sensors provide a sensor system signal incorporating the sleeping activity data, wherein the sleeping activity data includes at least heart rate data, respiratory rate data and patient body movement data.

The article "Sleep Assessment using a Passive Ballistocardiography-Based System: Preliminary Validation" by D. Mack et al., IEEE, pages 4319-4322 (2009) discloses a system for non-invasively analyzing physiological signals, which uses resilient pads placed on a bed to record minute movements associated with cardiac and respiratory functions, i.e. ballistocardiography, which is compared to actigraphy in distinguishing between sleep and wake periods.

The article "Comparison of actigraphy immobility rules with polysomnographic sleep onset latency in children and adolescents" by L. Meltzer et al., Sleep Breath, pages 1415-1423 (2015) evaluates different criteria of immobility as a measure of sleep onset latency in children and adolescents for determining the validity of actigraphy as an estimate of sleep-wake patterns.

SUMMARY OF THE INVENTION

It is thus an object of the present invention to provide a determination system and a determination method, which allow for a more reliable determination of a sleep stage of subject, in particular which improve the determination of the SOL of the subject.

In a first aspect of the present invention, a determination system for determining a sleep stage of a subject is provided. The determination system comprises a cardiorespiratory signal providing unit for providing a cardiorespiratory signal of the subject; an actigraphy data providing unit for providing actigraphy data of the subject; a first sleep stage determination unit for determining the sleep stage of the subject based on the cardiorespiratory signal of the subject; a second sleep stage determination unit for determining the sleep stage of the subject based on the actigraphy data of the subject; and a determination control unit for determining one out of the first sleep stage determination unit and the second sleep stage determination unit for determining the sleep stage of the subject. The first sleep stage determination unit is configured to determine a SOL of the subject. The determination control unit is configured to determine the sleep stage of the subject using the first sleep stage determination unit up to the SOL and to determine the sleep stage of the subject using the second sleep stage determination unit after the SOL.

Since the first sleep stage determination unit is configured to determine a SOL of the subject, wherein the first sleep stage determination unit is configured to determine the sleep stage based on the cardiorespiratory signal, the underestimation of the SOL occurring with actigraphy based SOL estimates can be improved. Further, since the determination system by means of the determination control unit is configured to determine the sleep stage of the subject using the second sleep stage determination unit after the SOL, the advantages of the second sleep stage determination unit, which is configured for determining the sleep stage of the subject based on actigraphy data, can be exploited. Accordingly, the determination system according to the invention improves the determination of the SOL, while the accuracy of the sleep stage determination for the subject, such as during the entire night, is maintained.

Preferentially, a sleep stage of the subject can be a discrimination among a sleep and wake state of the subject. Further preferentially, the sleep state of the subject can be further differentiated in a plurality of sleep stages, such as stages 1 to 4 and REM (rapid eye movement) as known in the art. Yet, also other sleep stage classifications are contemplated.

The cardiorespiratory signal providing unit can be a storing unit, in which the cardiorespiratory signal is stored already, wherein the cardiorespiratory signal providing unit can be adapted to provide the stored cardiorespiratory signal. However, the cardiorespiratory signal providing unit can also be a receiving unit for receiving a cardiorespiratory signal from a cardiorespiratory signal measurement unit such as a cardiorespiratory sensor and for providing the received cardiorespiratory signal. Moreover, the cardiorespiratory signal providing unit can be the cardiorespiratory signal measurement unit itself, wherein the cardiorespiratory signal providing unit provides the measured cardiorespiratory signal.

Likewise, the actigraphy data providing unit can be a storing unit, in which the actigraphy data is stored already, wherein the actigraphy data providing unit can be adapted to provide the stored actigraphy data. However, the actigraphy data providing unit can also be a receiving unit for receiving a actigraphy data from a actigraphy measurement unit and for providing the received actigraphy data. Moreover, the actigraphy data providing unit can be the actigraphy measurement unit itself, wherein the actigraphy data signal providing unit provides the measured actigraphy data.

Preferentially, the cardiorespiratory signal and the actigraphy data are synchronous signals and correspond to the same time periods. Further preferentially, the cardiorespiratory signal and the actigraphy data correspond to at least a part of a phase during which the subject intends to sleep, more preferably to the complete night, during which the subject intends to sleep. The cardiorespiratory signal and the actigraphy signal preferentially comprise an indicator of time, wherein a time period or epoch of the signal, for instance, and without being limited, of several seconds to minutes, can be determined from the cardiorespiratory signal and the actigraphy signal, respectively, based on the indicator of time.

Preferentially, the first sleep stage determination unit and/or the second sleep stage determination unit are configured to determine the sleep stage for a certain epoch of the cardiorespiratory signal and/or the actigraphy signal. Further preferentially, the first sleep stage determination unit and/or the second sleep stage determination unit are configured to divide the cardiorespiratory signal and/or the actigraphy data into multiple epochs and to determine the sleep stage of the subject for the respective epoch.

An epoch has preferably a duration of between 1 second and 5 minutes, more preferably between 10 seconds and 1 minute and most preferably about or exactly 30 seconds. However, in other embodiments, also other durations for epochs are contemplated.

Preferentially, the SOL is determined by the first sleep stage determination unit as the amount of time before a certain criterion is determined, for instance, until the first occurrence of a predefined number of consecutive epochs classified as sleep by the first sleep stage determination unit. Preferentially, the predefined number of consecutive epochs classified as sleep is set to 3, wherein higher or lower numbers are advantageously possible in other embodiments.

The first sleep stage determination unit, the second sleep stage determination unit and the determination control unit can in one embodiment be provided in one or more processors that are arranged in the same or different physical devices. More precisely, the first sleep stage determination unit, the second sleep stage determination unit and the determination control unit can in one embodiment be provided together with the cardiorespiratory signal providing unit and the actigraphy signal providing unit as the determination system in a single device or in a different embodiment be distributed over multiple devices.

In one embodiment the first sleep stage determination unit and the second sleep stage determination unit are adapted for communicating with the cardiorespiratory signal providing unit and/or the actigraphy signal providing unit in a wired or wireless manner as well known in the art. In one embodiment, one, more or all of the first sleep stage determination unit, the second sleep stage determination unit and the determination control unit are provided at a server, which is arranged for communicating with the rest of the determination system by suitable communication means, for instance via the Internet. In an embodiment of the determination system, the first sleep stage determination unit is configured to be irrespective of the actigraphy data.

Since the first sleep determination unit is configured to be irrespective of the activity data, and since the first sleep stage determination unit is configured to determine the SOL of the subject, body movements that underlie the actigraphy data are explicitly avoided for determining the SOL. Accordingly, accuracy of SOL determination can be improved, even for subjects that show a high SOL and try to lie as still as possible when trying to fall asleep. In other words, in this embodiment the determination of the first sleep stage determination unit does not rely on actigraphy data.

In an embodiment of the determination system, the second sleep stage determination unit is configured to determine the sleep stage of the subject based on the actigraphy data of the subject and based on the cardiorespiratory signal of the subject.

The second sleep stage determination unit can determine the sleep stage of the subject based on the actigraphy data and based on the cardiorespiratory signal as in this embodiment, or even based on the actigraphy data, the cardiorespiratory signal and further data in another embodiment. Since the sleep stage of the subject is determined using the second sleep stage determination unit after the SOL, i.e. while the subject has already fallen asleep, the combination of cardiorespiratory signal and actigraphy data can provide a sleep stage determination with high accuracy.

In an embodiment of the determination system, the cardiorespiratory signal providing unit is configured to provide a cardiac signal and/or a respiratory signal.

The cardiorespiratory signal providing unit thus can provide a cardiac signal only, a respiratory signal only or both a cardiac signal and a respiratory signal. A cardiac signal is a signal, in which cardiac features of the subject are detectable, such as heartbeats et cetera. A respiratory signal is a signal in which features of the respiratory system are detectable, such as respiration rate and amplitude. It is known that a single signal can comprise both cardiac features and respiratory features, such that a single signal can be both a cardiac signal and a respiratory signal. However, in other embodiments, the cardiorespiratory signal providing unit is configured to provide a separate cardiac signal and a separate respiratory signal, which are indicative of cardiac features or respiratory features, respectively.

In an embodiment of the determination system, the cardiorespiratory signal providing unit comprises a cardiorespiratory signal measurement unit including at least one of electrocardiographic (ECG) sensors, photoplethysmographic (PPG) sensors, ballistocardiography (BCG) sensors, respiratory inductance plethysmography (RIP) sensors, thermistor cannula sensors and Doppler radar sensors.

Since in this embodiment the cardiorespiratory signal providing unit comprises a cardiorespiratory measurement unit, the cardiorespiratory signal providing unit can measure and directly provide the cardiorespiratory signal of the subject.

ECG sensors are known and are traditionally mounted on the chest of the subject. ECG sensors comprise electrodes which are arranged for detecting electrical changes on a skin of the subject originating from the electrical activity of the heart. PPG sensors are known to comprise one or more light sources for illuminating a part of the subject's body and one or several detectors for detecting the light from the subject's body, wherein the cardiorespiratory measurement unit is preferentially adapted to determine the cardiorespiratory signal based on the PPG based on the detected light. In a preferred embodiment, the PPG sensors are mountable on the wrist or the finger-tip of the subject. BCG sensors are not in contact with the subjects, but, for instance, comprise load or pressure sensors mounted on top of or under the mattress the subject lies on during sleep.

Preferentially, a cardiorespiratory signal measured using PPG sensors and/or BCG sensors provide both cardiac features and respiratory features.

Doppler radar sensors can be provided distant from the subject, for instance, mounted on the ceiling or provided on a night table adjacent the bed, and are arranged for deriving velocities of motion of the subject from frequency changes of radar waves emitted from the sensors and reflected back to the sensors from the subject.

RIP sensors preferentially comprise insulated wire coils such as sinusoidal shaped wire coils, which are placed on the chest of the subject, wherein respiratory information is deduced from the change in self inductance of the coils and the frequency of their oscillation during respiration.

Alternatively or additionally, a cardiorespiratory signal can also be measured by means of respiratory flow using the thermistor cannula sensors. Preferentially, the cannula sensors are placed on the nose and/or mouth of the subject.

In an embodiment, the cardiorespiratory signal measurement unit is configured to provide the cardiorespiratory signal and actigraphy data. In this embodiment, the signal measurement unit preferentially includes BCG sensors or Doppler radar sensors. Preferentially, since the cardiorespiratory signal provided by the cardiorespiratory signal measurement unit can further comprise features indicative of body motion of the subject, i.e. actigraphy data, the actigraphy data providing unit can preferentially be configured to provide actigraphy data based on the cardiorespiratory signal.

Although ECG sensors, PPG sensors, BCG sensors, RIP sensors, thermistor cannula sensors and Doppler radar sensors are provided as preferred examples for sensors included in the cardiorespiratory signal measurement unit, in other examples also other forms of sensors can advantageously be included in the cardiorespiratory signal measurement unit.

In an embodiment of the determination system, the actigraphy data providing unit comprises a actigraphy measuring unit including accelerometers attachable to the body of the subject.

Accelerometers attachable to the body directly measure accelerations and thus motion of the body, respectively the body parts of the subject the accelerometers are attached to, and provide a measured actigraphy data signal.

Additionally or alternatively, the actigraphy measuring unit can also comprise BCG sensors, Doppler radar sensors or PPG sensors which are configured to determine accelerations and/or motion of at least parts of the body of the subject. Preferentially, the actigraphy measuring unit and the cardiorespiratory signal measurement unit can rely on the same sensors. However, in other embodiments, also separate sensors for the actigraphy measurement unit and the cardiorespiratory signal measurement unit can be provided.

In an embodiment of the determination system, the actigraphy measuring unit is a wrist-worn device.

Subjects are used to wear wrist-worn devices and wrist-worn devices are of little obtrusion to the subject. This is particularly advantageous, since obtrusive measuring units can impede the subject from sleeping, which is, however, contradicting the topic of interest.

In an embodiment, the determination system further comprises a cardiorespiratory signal feature extraction unit for extracting at least one of i) one or more cardiac features, ii) one or more respiratory features, and iii) one or more cardiorespiratory coupling features from the cardiorespiratory signal. At least one of the first sleep stage determination unit and the second sleep stage determination unit is configured to determine the sleep stage of the subject based on one or more of the extracted i) one or more cardiac features, ii) one or more respiratory features, and iii) one or more cardiorespiratory coupling features.

Since preferably the features extracted by the cardiorespiratory signal feature extraction unit are discriminative of sleep and wake, or more generally of a sleep stage of the subject, the determination of the sleep stage by the first sleep stage determination unit and/or the second sleep stage determination unit can be improved.

In an embodiment of the determination system, the cardiorespiratory signal feature extraction unit is configured to extract at least one of: cardiac features based on a heartbeat, such as R-R intervals based on an electrocardiographic signal or beats detected from a PPG signal, respiratory features based on a respiration rate or a respiration amplitude, and cardiorespiratory coupling features based on a coupling between cardiac and respiratory system, such as including a phase synchronization between heartbeat and respiratory phase.

In this embodiment, the cardiorespiratory signal feature extraction unit preferentially extracts particular cardiac features, respiratory features and/or cardiorespiratory coupling features which are discriminative of different sleep stages of the subject. Although cardiac features based on a heartbeat, respiratory features based on a respiration rate or a respiration amplitude and cardiorespiratory coupling features based on a coupling are provided as examples of cardiac features, respiratory features and cardiorespiratory coupling features, also other suitable discriminative features are contemplated by the skilled person.

In an embodiment of the determination system, the first sleep stage determination unit comprises a first sleep stage classification subunit. The first sleep stage classification subunit is configured to classify the sleep stage of the subject based on at least one of i) one or more cardiac features ii) one or more respiratory features, and iii) one or more cardiorespiratory coupling features extracted by the cardiorespiratory signal feature extraction unit extracted by the cardiorespiratory signal feature extraction unit. The second sleep stage determination unit comprises a second sleep stage classification subunit. The second sleep stage classification subunit is configured to classify the sleep stage of the subject based on the actigraphy data and optionally based on at least one of i) one or more cardiac features ii) one or more respiratory features, and iii) one or more cardiorespiratory coupling features extracted by the cardiorespiratory signal feature extraction unit.

Since the first sleep stage determination unit comprises a first sleep stage classification subunit, the sleep stage of the subject can be classified based on one or more extracted features. The one or more extracted features can, for instance, be determined during a training phase for the first sleep stage classification subunit and the second sleep stage classification subunit. In other embodiments, the one or more extracted features can also be predetermined and/or be provided by the subject. The set of features used for the first sleep stage classification subunit preferentially differs from the set of features used for the second sleep stage classification subunit.

In an embodiment, the set of features used for the first sleep stage classification subunit and/or the second sleep stage classification subunit is determined with any one of feature selection algorithms known from literature, for instance, the correlation feature selection shown in Hall, Mark A. 1999. "*Correlation-Based Feature Selection for Machine Learning.*" The University of Waikato. However, in other embodiments, the set of features can also be determined by different algorithms or manually.

Preferentially, the first sleep stage classification subunit and/or the second sleep stage classification subunit are a classifier described in literature, such as a Bayesian linear discriminant classifier for each of the epochs or time periods. This classifier is, for instance, discussed in Devot, S., R. Dratwa, and E. Naujokat. Sleep/wake detection based on cardiorespiratory signals and actigraphy. In: Proc. 2010 Annu. Int. Conf. IEEE Eng. Med. Biol. Soc., 2010. However, also other classifiers known in the art are contemplated by the person skilled in the art.

In an embodiment, the determination system further comprises a training unit for training the first sleep stage classification subunit and the second sleep stage classification subunit. The training unit comprises a cardiorespiratory training signal providing subunit for providing at least one of a cardiac training signal and a respiratory training signal as a cardiorespiratory training signal, an actigraphy training data providing subunit for providing actigraphy training data, a reference annotations providing subunit for providing the sleep stage corresponding to the cardiorespiratory training signal and the actigraphy training data as reference data. The cardiorespiratory signal feature extraction unit is configured to extract at least one of one or more cardiac features and one or more respiratory features from the cardiorespiratory training signal. The training unit is configured to train the first sleep stage classification subunit based on the extracted cardiac features and respiratory features and the reference data, and wherein the training unit is configured to train the second sleep stage classification subunit based on the actigraphy training data and the reference data.

Preferentially, the reference data comprises the true sleep stage of the subject during the period, to which the cardiac training signal, the respiratory training signal and/or the actigraphy training data relate. For instance, reference data comprises ground truth annotations such as sleep and wake epochs and SOL provided by an expert.

Advantageously, the training unit yields the result that the first sleep stage classification subunit and the second sleep stage classification subunit are trained to provide an optimized model for different classifiers. In other words, since the classifier implemented in the first sleep stage classification subunit includes a list of cardiac and/or respiratory features, this classifier is optimized for determining the SOL by the training unit. Further, since the classifier implemented in the second sleep stage classification subunit comprises actigraphy data and is trained on actigraphy training data, this classifier is optimized by the training unit for determining a sleep stage after the SOL.

In an embodiment of the determination system, the training unit is configured to train the second sleep stage classification subunit based on the extracted cardiac features and respiratory features, the actigraphy training data and the reference data.

Since in this embodiment the second sleep stage classification subunit implements a model of a classifier including the extracted cardiac features and respiratory features along with the actigraphy training data, the determination of the sleep stage of the subject can be improved for a period following the SOL.

In an embodiment of the determination system, the training unit is configured to train the first sleep stage classification subunit based on a subpart of the data corresponding to a first time period only.

Preferentially, the subpart of the data corresponding to a first time period corresponds to the first minutes after the subject starts to intent to fall asleep. Preferably, the first time period has a duration which exceeds the SOL for most subjects. In one instance, the first time period includes a length of about 90 minutes. However, in other embodiments, also different, i.e. longer or shorter, time periods for the first time period are advantageously possible.

Since the first sleep stage classification subunit is trained using the subpart of the data containing the SOL, the first sleep stage classification subunit is further optimized for determining the SOL, since the amount of training data not comprising the SOL is reduced. Thus, training with less suitable time periods, i.e. the periods not containing the SOL, is reduced.

In another embodiment, the training unit is configured to train the second sleep stage classification subunit based on a subpart of the data corresponding to a second time period only. Preferentially, the second time period corresponds to the remaining time period, which remains after the first time period has past. Thereby, the second sleep stage classification subunit is optimized for the period during which the subject is at sleep. However, in other embodiments, the first and second time periods can also overlap to some extent, wherein preferably only the first time period contains the time corresponding to the SOL.

In an embodiment of the determination system, the determination system is configured to determine the sleep stage of the subject using the first sleep stage determination unit after determining the subject sleep stage to be awake for a time period following the SOL. In this embodiment, when the determination system determines that the subject awakes after having been asleep for a certain period of time, i.e. after the SOL, the first sleep stage determination unit is selected to determine the sleep stage of the subject again. Further preferentially, the determination system can be configured to further determine the sleep stage of the subject using the second sleep stage determination unit after a new sleep onset latency, i.e. the subject falling asleep another time, is determined. Further preferentially, this process can be repeated as many times as the sleep stage of the subject is determined to change from awake to sleep and vice versa.

In a further aspect of the invention a determination method for determining a sleep stage of a subject is provided. The determination method comprises: providing a cardiorespiratory signal of the subject; providing actigraphy data of the subject; determining the sleep stage of the subject based on the cardiorespiratory signal of the subject using a first sleep stage determination unit; and determining the sleep stage of the subject based on at least the actigraphy data of the subject using a second sleep stage determination unit. The first sleep stage determination unit is configured to determine a SOL of the subject. The sleep stage of the subject is determined using the first sleep stage determination unit up to the SOL and is determined using the second sleep stage determination unit after the SOL.

In a further aspect of the invention a computer program for determining a sleep stage of a subject is provided. The computer program comprises program code means for causing a determination system as defined in claim 1 to carry out the determination method as defined in claim 14, when the computer program is run on the determination system.

It shall be understood that the determination system for determining a sleep stage of a subject of claim 1, the determination method for determining a sleep stage of a subject of claim 14 and the computer program for determining a sleep stage of a subject of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
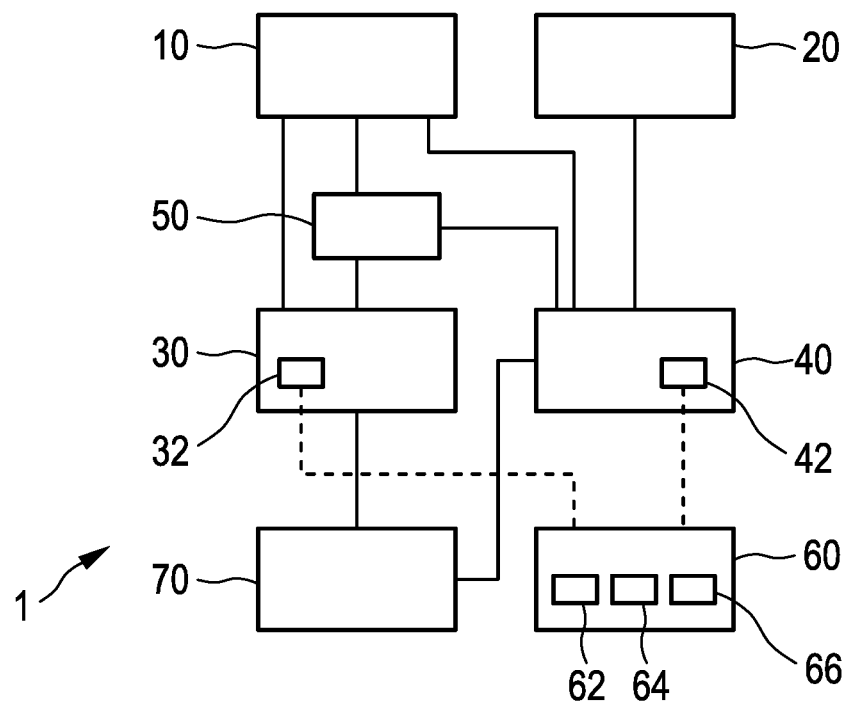
FIG. 1 schematically and exemplarily shows an embodiment of a determination system for determining a sleep stage of a subject, FIG. 2 schematically and exemplarily shows an embodiment of a determination method for determining a sleep stage of a subject.

FIG. 1 schematically and exemplarily shows an embodiment of a determination system 1 for determining a sleep stage of a subject. Determination system 1 comprises a cardiorespiratory signal providing unit 10, an actigraphy data providing unit 20, a first sleep stage determination unit 30, a second sleep stage determination unit 40, a cardiorespiratory signal feature extraction unit 50, a training unit 60 and a determination control unit 70.

Cardiorespiratory signal providing unit 10 is configured to provide a cardiorespiratory signal of the subject to first sleep stage determination unit 30 and in this example also to cardiorespiratory signal feature extraction unit 50 and second sleep stage determination unit 40. The cardiorespiratory signal is indicative of cardiac activity and/or respiratory activity of the subject.

In this example, cardiorespiratory signal providing unit 10 comprises sensors for measuring cardiac activity and respiratory activity. For instance, cardiac activity can be measured with ECG sensors traditionally mounted on the chest of the subject, with PPG sensors mounted for example on the wrist or the finger tip of the subject, or by means of BCG sensors, e.g. with load or pressure sensors mounted on top of or under the mattress. Further, in this example, respiratory activity is measured with RIP sensors usually mounted on belts worn around the thorax or abdomen, or with BCG sensors which are also indicative of cardiac activity. A further example would be Doppler radar sensors, which are mounted on, for instance, the night table. In a further example, which does not rely on measuring respiratory motion being indicative of respiratory effort, for measuring respiratory activity, cardiorespiratory signal providing unit 10 comprises sensors for measuring respiratory flow, such as, for instance, thermistor cannula sensors which are mountable on the nose and/or mouth of the subject.

Actigraphy data providing unit 20 provides actigraphy data of the subject to second sleep stage determination unit 40. Actigraphy data proving unit 20 does not provide actigraphy data to first sleep stage determination unit 30, since first sleep stage determination unit 30 is irrespective to actigraphy data, i.e. does not rely on actigraphy data. Actigraphy in general measures gross body movements and is usually determined with accelerometers mounted on the body, for instance using wrist worn devices or with sensors on the bed the subject lies in, for instance, pressure sensors, Doppler radar sensors, which also provide a signal indicative of respiratory activity, or the like.

First sleep stage determination unit 30 is configured to determine the sleep stage of the subject based on the cardiorespiratory signal of the subject only. Second sleep stage determination unit 40 is configured to determine the sleep stage of the subject based on the actigraphy data of the subject, and, in this example, also based on the cardiorespiratory signal. The use of cardiorespiratory information improves the accuracy of sleep/wake estimation, but, however, since sleep/wake classifiers used for sleep/wake determination still make use of body movements, i.e. actigraphy, or albeit together with cardiorespiratory activity, SOL is still underestimated. For this reason, first sleep stage determination unit 30, which does not rely on actigraphy data, i.e. body movements of the subject, is configured to determine the SOL of the subject. Determination control unit 70 is configured for determining one out of first sleep stage determination unit 30 and second sleep stage determination unit 40 for determining the sleep stage of the subject, more precisely to determine the sleep stage of the subject using first sleep stage determination unit 10 up to the SOL time and to determine the sleep stage of the subject using second sleep stage determination unit 40 after the SOL.

Cardiorespiratory signal feature extraction unit 50 is configured to extract at least one of one or more cardiac features and one or more respiratory features from the cardiorespiratory signal. Several cardiac features have been shown, for instance as published in Fonseca, Pedro, Xi Long, Mustafa Radha, Reinder Haakma, Ronald M Aarts, and Jerome Rolink. 2015. "*Sleep Stage Classification with ECG and Respiratory Effort.*" IOP Physiological Measurement 36: 2027-40, to be discriminative of sleep and wake or in general different sleep stages. Several cardiac features are based on statistics computed over R-R intervals calculated from ECG or on beats detected from a PPG signal. Features can be calculated such as the number of intervals per epoch, i.e. a time period, and express the average heart rate in that epoch. Further features include, for instance, the nth percentile, a standard deviation and the range of the interval lengths. Other features can describe characteristics resulting from power spectral density (PSD) analysis, which are computed over multiple frequency bands. In one example, PSD analysis is carried out over three different frequency bands: very low frequency (VLF), 0.005-0.04 Hz, low frequency (LF) 0.04-0.15 Hz and high frequency (HF) 0.15-0.45 Hz, and from the modulus and the phase of the pole in the high frequency band. However, in other examples, also other frequency bands and/or other mathematical methods are feasible. Other measures capture the regularity of the signal over different time scales, for instance, detrended fluctuation analysis (DFA) can be employed to identify longer term correlations in the signal, and sample entropy to quantify the self similarity of the signal over a given time period. Some features can be particularly relevant for sleep stage detection, wherein others can be particularly used for wake detection.

Also several respiratory features can be discriminative of sleep and wake, or in general, different sleep stages. Respiration rate and amplitude are linked to different sleep stages. In particular, a variation of respiration rate over several epochs can help distinguish wake, non-rapid eye movement (NREM) sleep and rapid eye movement (REM) sleep. Different properties of respiratory effort amplitude can be more regular during deep sleep than in other stages and can also help discriminate NREM and REM. Further, self similarity measurements using dynamic warping can be useful for detecting wake states.

Besides cardiac and respiratory activity being analyzed separately, cardiorespiratory coupling features describe the strength of coupling between cardiac and respiratory autonomic systems and the strength of this link depends on the sleep stage. Features describing cardiorespiratory coupling include the phase synchronization between RR intervals from ECG or beats from PPG and the respiratory phase measure from RIP or from PPG during a number of breathing cycles.

Two sets of features provided by cardiorespiratory signal feature extraction unit 50 and, in case of second sleep stage determination unit 40 also by actigraphy data providing unit 20, will be used to classify the sleep stage in distinct periods of the signals, such as during different periods of the night. More precisely, the first set will be used before SOL and the second set will be used after SOL.

In this respect, first sleep stage determination unit 30 comprises a first sleep stage classifying subunit 42 and second sleep stage determination unit 40 comprises a second sleep stage classifying subunit 42. First and second sleep stage classifying subunits 32, 42 are configured to classify the sleep stage of the subject based on the respective set of features, which can be determined by hand, or more commonly, determined with a feature selection algorithm, such as correlation feature selection described in Hall, Mark A. 1999. "*Correlation-Based Feature Selection for Machine Learning.*" The University of Waikato.

Provided with the respective feature set, first and second sleep stage classifying subunits 32 and 42 can be trained with example data of distinctive periods of the cardiorespiratory signal and the actigraphy data, respectively. For instance, a Bayesian linear discriminant classifier can be used for each of these periods, wherein different classifiers can be employed in other examples.

For training first and second sleep stage classifying subunit 32, 42, training unit 60 comprises a cardiorespiratory training signal providing subunit 62, which provides at least one of a cardiac training signal and a respiratory training signal, an actigraphy training data providing subunit 64 which provides actigraphy training data, and a reference annotations providing subunit 66,which provides the sleep stage corresponding to the respiratory training signal and the actigraphy training data as reference data. Reference data provides the correct classification of the sleep stage for a certain epoch, as annotated, for instance, by an expert. An exemplary training process will be described with reference to FIG. 3 below. A subsequent classification process will exemplarily be described with reference to FIG. 4 below.

Figure 2:
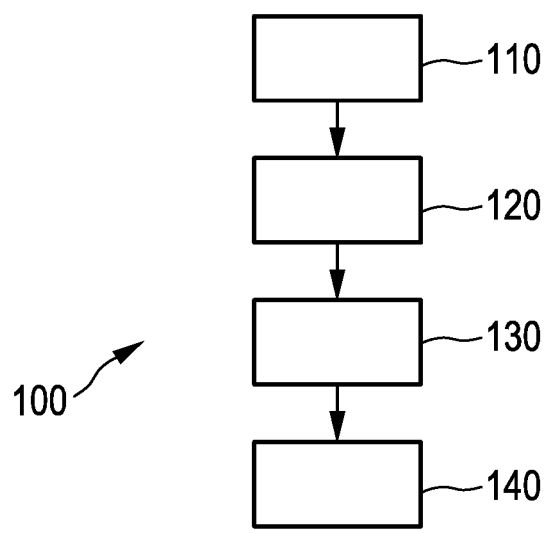

FIG. 2 schematically and exemplarily shows an embodiment of a determination method 100 for determining a sleep stage of a subject. Determination method 100 comprises a step of providing 110 a cardiorespiratory signal of the subject, a step of providing 120 actigraphy data of a subject, a step of determining 130 the sleep stage of the subject based on the cardiorespiratory signal of the subject using first sleep stage determination unit 30 as illustrated in FIG. 1. Finally, determination method 100 comprises a step of determining 140 the sleep stage of the subject based on at least the actigraphy data of the subject using second sleep stage determination unit 40. Determination method 100 can be implemented on determination system 1, as exemplarily shown in FIG. 1. In determination method 100, first sleep stage determination unit 30 is configured to determine a SOL of the subject, wherein determination method 100 determines 130 the sleep stage of the subject using the first sleep stage determination unit 30 up to the SOL and determines 140 the sleep stage of the subject using the second sleep stage determination unit 50 after the SOL.

Figure 3:
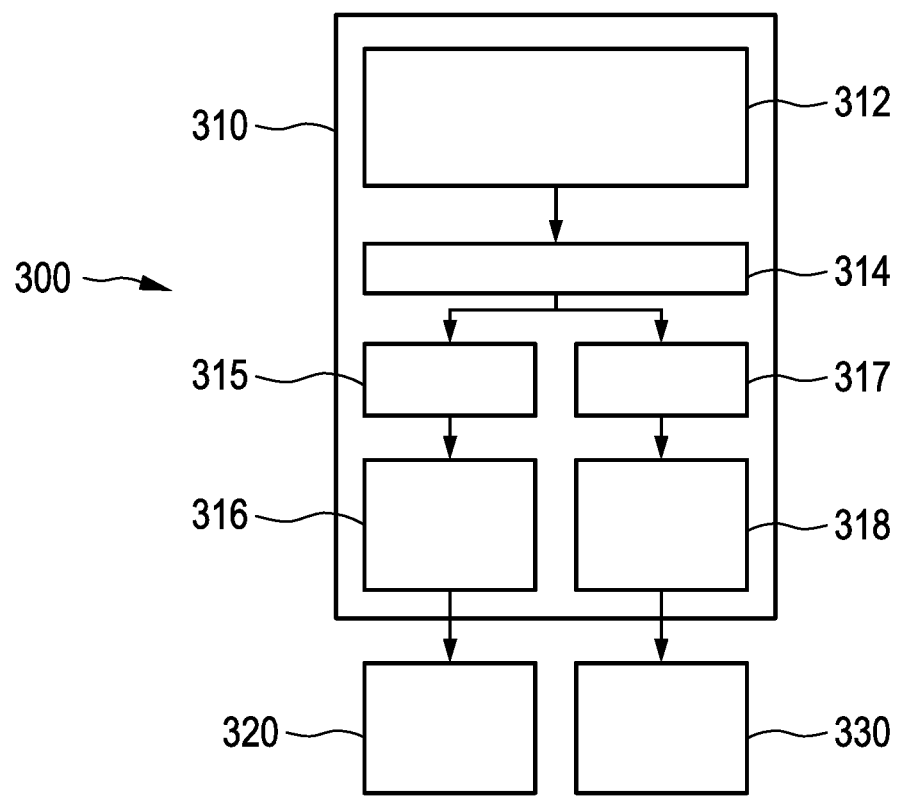
FIG. 3 shows a block diagram schematically and exemplarily illustrating a training method for training the determination system.

FIG. 3 shows a block diagram schematically and exemplarily illustrating a training method for training determination system 1. Training method 300 comprises a training subprocess 310, out of which a first classifier 320 and a second classifier 330 result. First classifier 320 can be implemented, for instance, in first sleep stage classifying subunit 32 and second classifier 330 can be implemented, for instance, in second sleep stage classifying subunit 42. The model for the first classifier 320 includes a list of cardiac and/or respiratory features, which are used during training (see below), the model for the second classifier 330 includes actigraphy and optionally cardiac and/or respiratory features used.

In a first step 312 of training subprocess 310 training data sets with sleep recordings including cardiac signals, and/or respiratory signals, along with actigraphy data and reference ground truth annotations data are provided. Reference ground truth annotations are, for instance, correct determinations of sleep stages annotated by, for instance, an expert, and comprises sleep and wake stage per epoch and the SOL. Cardiac signals are, for instance, ECG signals, PPG signals or the like. Respiratory signals include respiratory effort, respiratory flow, and the like. This data is provided, for instance, by cardiorespiratory training signal providing sub units 62, actigraphy training data providing sub units 64 and reference annotations providing sub unit 66.

Next, in step 340, cardiac and/or respiratory features are extracted, for example by means of cardiorespiratory signal feature extraction unit 50.

The method flow is split into two paths, in the left path in step 315, the recordings are cropped to the first one hour and 30 minutes. The other path, in step 317, the entire recordings are capped. The left path indicates the training for first sleep stage determination unit 20, and the right path defines the training method for second sleep stage determination unit 40. In this example, in step 315 the first one hour and 30 minutes are cropped, wherein in other examples also other time periods, such as longer or shorter periods, of the recording can be cropped.

Following the cropping in step 315, a first classifier is trained with cardiac and/or respiratory features in step 316. This training does not include actigraphy data or features. Thereby, an intended bias and underestimation of the SOL is reduced. In step 318, based on the complete recordings received in step 317, a second classifier is trained including actigraphy data. Optionally, also cardiac and/or respiratory features are included in the training in this step.

As indicated above, a model resulting from training in step 316 is provided for first sleep stage classifying subunit 32 in step 320 and a second model resulting from training in step 318 is provided to second sleep stage classifying subunit 42 in step 313.

The set of features in the first classifier 320 and the second classifier 330 are different. Avoiding the use of actigraphy data in the first classifier 320 to recognize periods before SOL increases the accuracy especially for a subject with long SOL. Since the movements, i.e. determinable in actigraphy data, occurring after sleep onset, during sleep, are involuntary, actigraphy is valuable during the period following sleep onset to detect awakenings and therefore it is included in the second classifier 330. First classifier 320 can also be applied to periods of long wakefulness during night, which are similar to periods before SOL and can be addressed with increased accuracy without including actigraphy data.

Figure 4:
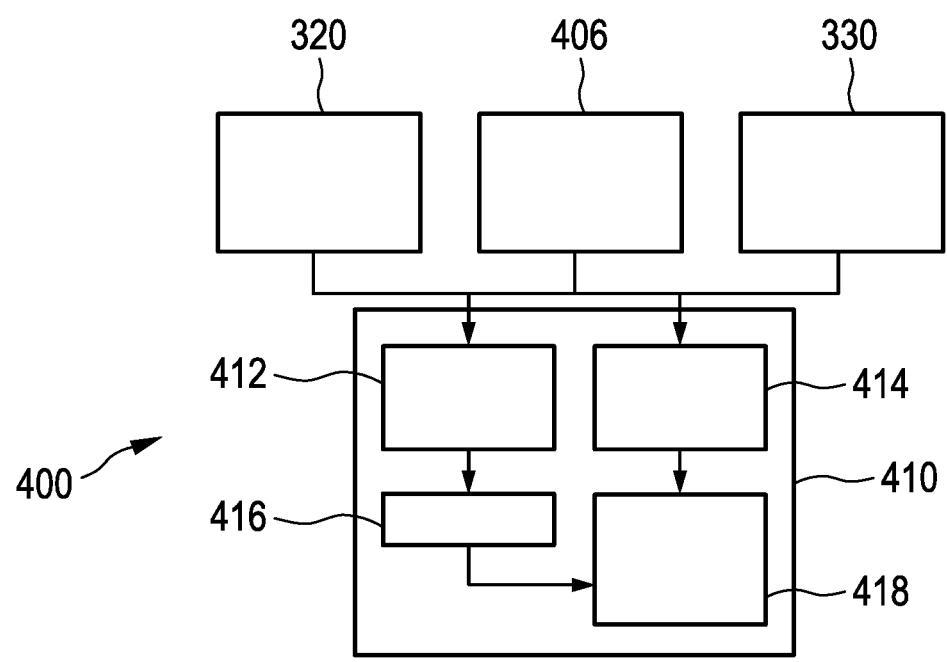
FIG. 4 shows a block diagram schematically and exemplarily illustrating a classification process, FIG. 5 schematically and exemplarily illustrates determination result of determining a SOL with a determination system according to the state of the art, and FIG. 6 schematically and exemplarily illustrates determination results of determining a SOL with the determination system according to the invention.

FIG. 4 shows a block diagram schematically and exemplarily illustrating a classification process 400 which comprises a classification main subprocess 410 and receives the first classifier 320 and the second classifier 330 as derived from the training process 300 of FIG. 3, and new recordings 406 including cardiac signals and/or respiratory signals together with actigraphy data. New recordings 406 are provided, for instance, by cardiorespiratory signal providing unit 10, and actigraphy data providing unit 20 of determination system 1. The input is further processed in step 412, in which cardiac and/or respiratory features for first classifier 320 are extracted. Parallel thereto in step 414, actigraphy, and optionally cardiac and/or respiratory features for second classifier 330 are extracted.

Following the extraction in step 412, first classifier 320 is used to detect the SOL in step 416.

Next, based on the SOL detection in step 416 and the features extracted in step 414, second classifier 330 is used in step 418 to classify sleep/wake and optionally sleep stages after SOL has been detected. In one example, classification process 400 is carried out by determination system 1.

Figure 5:
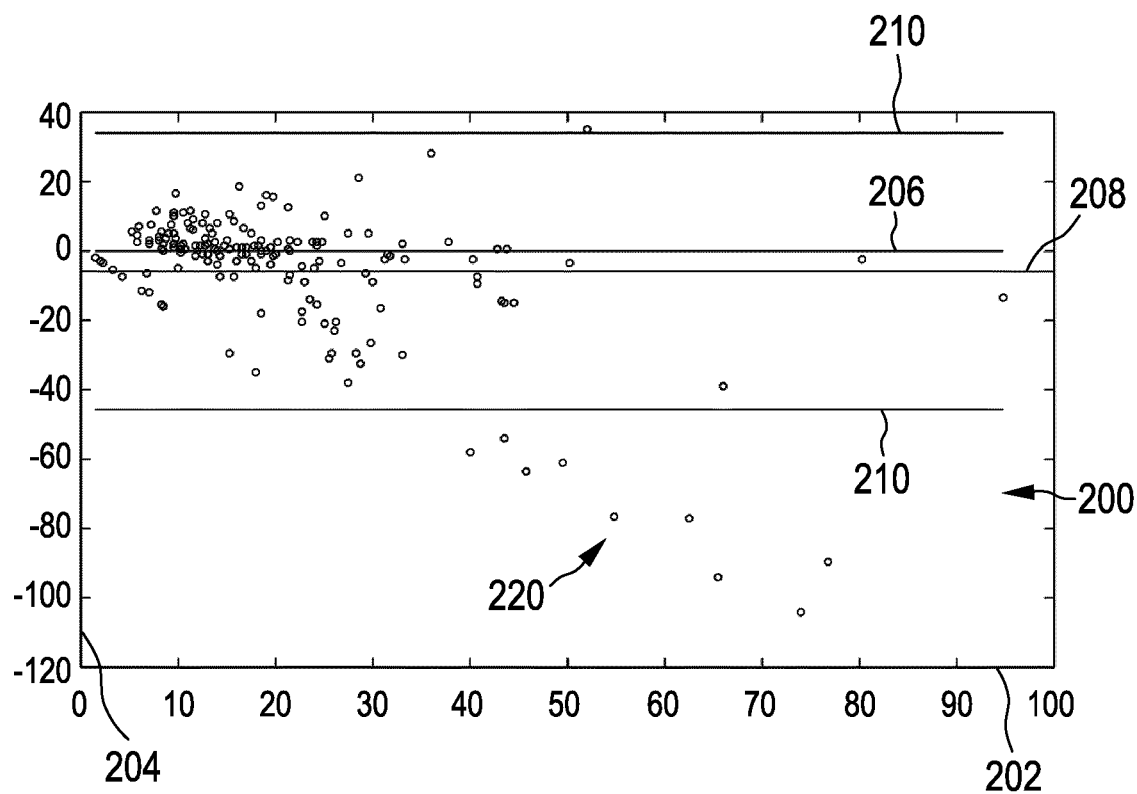
Figure 6:
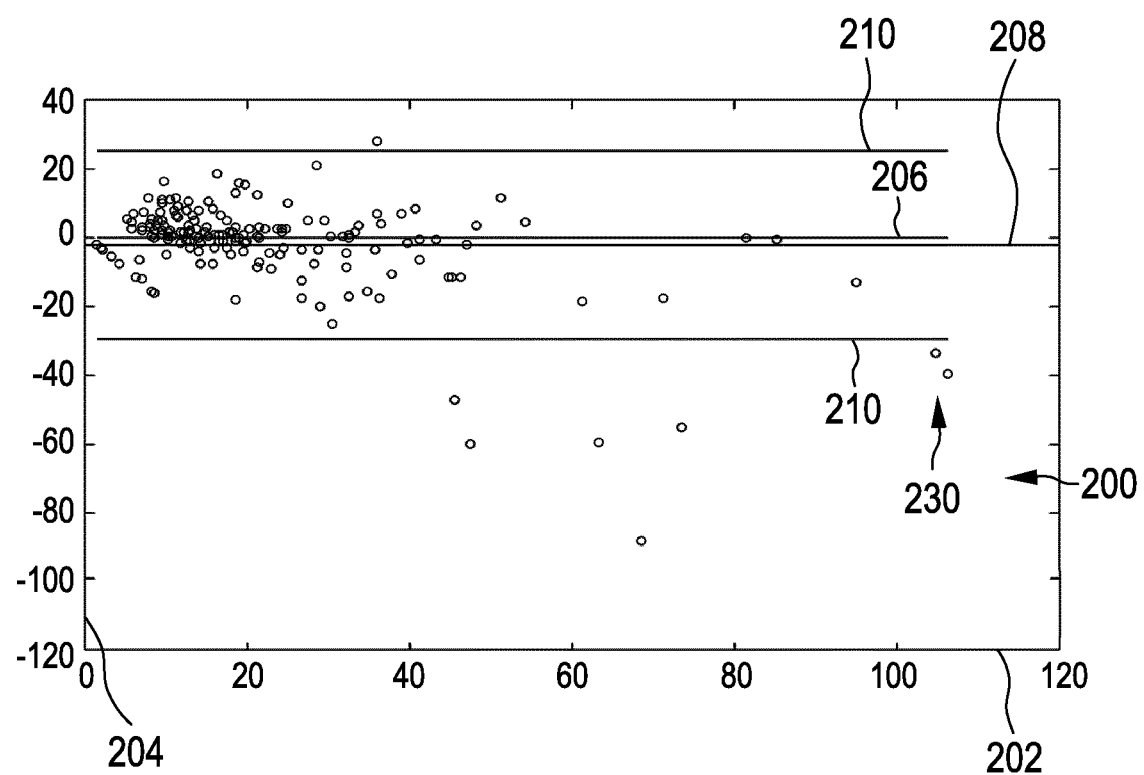

FIGS. 5 and 6 schematically and exemplarily illustrate plots 200 of determined SOLs using a determination system according to the state of the art in FIG. 5 and with determination system 1 according to the invention in FIG. 6. The plots 200 of FIGS. 5 and 6 are so-called Bland-Altman plots in this example.

In both plots 200, the average between an estimated SOL and a reference ground-truth SOL is shown on a horizontal axis 202, for instance, in a unit of minutes. On the vertical axis 204, a difference between estimated SOL and reference, i.e. correct, SOL is indicated, for instance also in the unit of minutes. Each circle in the plot represents a SOL estimate. Line 206 indicates the 0 difference line, i.e. SOL estimates on this line have no error and the estimated SOL corresponds to the reference SOL. Line 208 indicates the average difference of all estimated SOLs, and lines 210 indicate two times the standard deviation around the mean value represented by line 208. The two lines 210 are also called the 95% limits of agreement, since 95% of the points are comprised between the two lines 210. It can be seen that the SOL is generally underestimated, since mean value 208 lies below the 0 value 206 in both examples, in FIG. 5 and FIG. 6., for the reasons layed out above.

FIG. 5 shows very high errors particularly for large SOLs, which corresponds to the region next to the arrow indicated with reference sign 220.

Comparing FIG. 5 and FIG. 6, significant improvements using determination system 1 according to the present invention, which does not rely on actigraphy data for the first period for determining SOL, can be seen. First, the mean value 208 gets closer to the zero error line 206. This means, that determination system 1 according to the present invention significantly reduces the underestimation of the SOL. Further, lines 210 are closer to the mean 208, which essentially means that the standard deviation is reduced. It is particularly visible that for subjects with large SOL, such as SOL in the region indicated by arrow 230, the difference between estimated SOL and the reference SOL can significantly be reduced. Accordingly, determination system 1 according to the present invention yields overall improvements over known determination systems using actigraphy data for determining the SOL, wherein the improvements are in particular and most notable in the area of large SOLs, such as larger than 20 minutes.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. For example, although a first sleep stage determination unit and a second sleep stage determination unit have been described, also more than two sleep stage determination units may be used, wherein the determination control unit decides among the more than two sleep stage determination units according to definable criteria.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the determining the sleep stage of the subject based on the cardiorespiratory signal of the subject using a first sleep stage determination unit, and determining the sleep stage of the subject based on at least the actigraphy data of the subject using a second sleep stage determination unit et cetera performed by one or several units or devices can be performed by any other number of units or devices. These procedures and/or the control of the determination system for determining a sleep stage of a subject in accordance with determination method for determining a sleep stage of a subject can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The present invention thus relates to a determination system, a corresponding determination method and a computer program for determining a sleep stage of a subject. The determination system comprises a cardiorespiratory signal providing unit 10, an actigraphy data providing unit 20, a first sleep stage determination unit 30 for determining the sleep stage based on a cardiorespiratory signal, and a second sleep stage determination unit 40 for determining the sleep stage based on actigraphy data. The first sleep stage determination unit 30 determines a SOL of the subject. The sleep stage of the subject is determined using the first sleep stage determination unit 30 up to the SOL and the second sleep stage determination unit 40 after the SOL. The determination system and corresponding method allow for a more reliable determination of a sleep stage of subject, in particular improve the determination of the SOL of the subject.

The invention claimed is:

1. A determination system for determining a sleep stage of a subject, wherein the determination system comprises:
   a cardiorespiratory signal providing unit for providing a cardiorespiratory signal of the subject,
   an actigraphy data providing unit for providing actigraphy data of the subject,
   a first sleep stage determination unit for determining the sleep stage of the subject based on the cardiorespiratory signal of the subject and irrespective of the actigraphy data of the subject,
   a second sleep stage determination unit for determining the sleep stage of the subject based on the actigraphy data of the subject, and
   a determination control unit for selecting one out of the first sleep stage determination unit and the second sleep stage determination unit for determining the sleep stage of the subject,
      wherein the first sleep stage determination unit is configured to determine a sleep onset latency of the subject, and
      wherein the determination control unit is configured to determine the sleep stage of the subject using the first sleep stage determination unit until the first sleep stage determination unit determines the sleep onset latency of the subject, which causes the determination control unit to transition to determine the sleep stage of the subject using the second sleep stage determination unit.

2. The determination system of claim 1, wherein the second sleep stage determination unit is configured to determine the sleep stage of the subject based on the actigraphy data of the subject and based on the cardiorespiratory signal of the subject.

3. The determination system of claim 1, wherein the cardiorespiratory signal providing unit is configured to provide a cardiac signal and/or a respiratory signal.

4. The determination system of claim 1, wherein the cardiorespiratory signal providing unit comprises a cardiorespiratory signal measurement unit including at least one of electrocardiographic sensors, photoplethysmographic sensors, ballistocardiography sensors and Doppler radar sensors.

5. The determination system of claim 1, wherein the actigraphy data providing unit comprises an actigraphy measurement unit including accelerometers attachable to the body of the subject.

6. The determination system of claim 5, wherein the actigraphy measurement unit is a wrist-worn device.

7. The determination system of claim 1, further comprising a cardiorespiratory signal feature extraction unit for extracting at least one of i) one or more cardiac features, ii) one or more respiratory features, and iii) one or more cardiorespiratory coupling features from the cardiorespiratory signal, wherein at least one of the first sleep stage determination unit and the second sleep stage determination unit is configured to determine the sleep stage of the subject based on one or more of the extracted i) one or more cardiac features, ii) one or more respiratory features, and iii) one or more cardiorespiratory coupling features.

8. The determination system of claim 7, wherein the cardiorespiratory signal feature extraction unit is configured to extract at least one of:
   cardiac features based on a heartbeat, such as R-R intervals based on an electrocardiographic signal received from an electrocardiographic ("ECG") sensor or beats detected from a photoplethysmography ("PPG") signal received from a PPG sensor,
   respiratory features based on a respiration rate or a respiration amplitude, and
   cardiorespiratory coupling features based on a coupling between cardiac and respiratory system, such as including a phase synchronization between heartbeat and respiratory phase.

9. The determination system of claim 7, wherein the first sleep stage determination unit comprises a first sleep stage classification subunit, wherein the first sleep stage classification subunit is configured to classify the sleep stage of the subject based on at least one of i) one or more cardiac features ii) one or more respiratory features, and iii) one or more cardiorespiratory coupling features extracted by the cardiorespiratory signal feature extraction unit, and wherein the second sleep stage determination unit comprises a second sleep stage classification subunit, wherein the second sleep stage classification subunit is configured to classify the sleep stage of the subject based on the actigraphy data and based on at least one of i) one or more cardiac features, ii) one or more respiratory features, and iii) one or more cardiorespiratory coupling features extracted by the cardiorespiratory signal feature extraction unit.

10. The determination system of claim 9, further comprising a training unit for training the first sleep stage classification subunit and the second sleep stage classification subunit, wherein the training unit comprises:
    a cardiorespiratory training signal providing subunit for providing at least one of a cardiac training signal and a respiratory training signal as a cardiorespiratory training signal,
    an actigraphy training data providing subunit for providing actigraphy training data,
    a reference annotations providing subunit for providing the sleep stage corresponding to the cardiorespiratory training signal and the actigraphy training data as reference data,
    wherein the cardiorespiratory signal feature extraction unit is configured to extract at least one of i) one or more cardiac features and ii) one or more respiratory features from the cardiorespiratory training signal,
    wherein the training unit is configured to train the first sleep stage classification subunit based on the extracted cardiac features and respiratory features and the reference data, and wherein the training unit is configured to train the second sleep stage classification subunit based on the actigraphy training data and the reference data.

11. The determination system of claim 10, wherein the training unit is configured to train the second sleep stage classification subunit based on the extracted cardiac features and respiratory features, the actigraphy training data and the reference data.

12. The determination system of claim 10, wherein the training unit is configured to train the first sleep stage classification subunit based on a subpart of the data corresponding to a first time period only.

13. A determination method for determining a sleep stage of a subject, wherein the determination method comprises:
    providing a cardiorespiratory signal of the subject, providing actigraphy data of the subject, determining the sleep stage of the subject based on the cardiorespiratory signal of the subject, and irrespective of the actigraphy data of the subject, using a first sleep stage determination unit, and in response to determination, by the first sleep stage determination unit, of a sleep onset latency of the subject, determining the sleep stage of the subject based on at least the actigraphy data of the subject using a second sleep stage determination unit, wherein the first sleep stage determination unit determines a sleep onset latency of the subject, and wherein the sleep stage of the subject is determined using the first sleep stage determination unit until the first sleep stage determination unit determines the sleep onset latency of the subject, which causes a transition to using the second sleep stage determination unit.

14. At least one non-transitory computer-readable medium comprising instructions that, in response to execution of the instructions by one or more processors, cause the one or more processors to perform the following operations to determine a sleep stage of a subject:

providing a cardiorespiratory signal of the subject, providing actigraphy data of the subject, determining the sleep stage of the subject based on the cardiorespiratory signal of the subject, and irrespective of the actigraphy data of the subject, using a first sleep stage determination unit, and in response to determination, by the first sleep stage determination unit, of a sleep onset latency of the subject, determining the sleep stage of the subject based on at least the actigraphy data of the subject using a second sleep stage determination unit, wherein the first sleep stage determination unit determines a sleep onset latency of the subject, and wherein the sleep stage of the subject is determined using the first sleep stage determination unit until the first sleep stage determination unit determines the the sleep onset latency of the subject, which causes a transition to using the second sleep stage determination unit.

15. The determination system of claim 1, wherein the first sleep stage determination unit comprises a first classifier that is optimized by a training unit for determining sleep onset latency of subjects generally based on cardiorespiratory signals, and wherein the second sleep stage determination unit comprises a second classifier, distinct from the first classifier, that is optimized by the training unit for determining the sleep state of subjects generally after sleep onset latency.

* * * * *